United States Patent [19]

Nachman et al.

[11] Patent Number: 5,792,466
[45] Date of Patent: Aug. 11, 1998

[54] MIMETIC INSECT KININ ANALOGS FOR INSECT CONTROL

[75] Inventors: Ronald J. Nachman, Willis; Grant Mark Holman, Bryan, both of Tex.

[73] Assignee: The United States of America, as represented by the Secretary of Agriculture, Washington, D.C.

[21] Appl. No.: 766,703

[22] Filed: Dec. 13, 1996

[51] Int. Cl.$^6$ .................................................. A01N 25/02
[52] U.S. Cl. ...................... 424/405; 424/406; 514/17; 514/18; 514/803; 530/330; 930/20; 930/320
[58] Field of Search .................................. 424/405, 838, 424/406; 514/17, 18, 803; 930/20, 140, 320, DIG. 784, 800, 802; 530/330

[56] References Cited

U.S. PATENT DOCUMENTS 5,589,460  12/1996  Abajian et al. ........................ 574/17

*Primary Examiner*—Neil S. Levy
*Attorney, Agent, or Firm*—M. Howard Silverstein; Randall E. Deck; John D. Fado

[57] ABSTRACT

Novel pseudopeptide analogs of the insect kinin neuropeptide family which possess biological activity mimicking that of the naturally occurring neuropeptides are disclosed. By substituting a sterically hindered amino acid which is compatible with a turn conformation, for the $Xaa^2$ amino acid of the insect kinin C-terminal pentapeptide (i.e. Ser, Pro, or Ala), analogs are produced which exhibit resistance to degradation by angiotensin converting enzyme (ACE) while still retaining biological activity. The analogs may be used for insect control by disrupting the diuretic and/or myotropic activity in insects.

18 Claims, 2 Drawing Sheets

MIMETIC INSECT KININ ANALOGS FOR INSECT CONTROL

BACKGROUND OF THE INVENTION

1. Field of Invention

This invention relates to mimetic pseudopeptide analogs of the insect kinin neuropeptide family, and the use of these analogs for insect control.

2. Description of the Prior Art

The insect kinin neuropeptide family shares the common C-terminal pentapeptide Phe—Xaa$^1$—Xaa$^2$—Trp—Gly—NH$_2$ (Xaa$^1$=His, Asn, Phe, Ser, or Tyr; Xaa$^2$=Ser, Pro, or Ala) and has been isolated from such diverse sources as the cockroach *Leucophaea maderae* [Holman, et al., 1987, Comp. Biochem. Physiol. [C], 88(1):31–34] cricket *Acheta domesticus* [Holman et al., A strategy for the isolation and structural characterization of certain insect myotropic peptides that modify spontaneous contractions of the isolated cockroach hindgut, In: Chromatography and isolation of insect hormones and pheromones, McCaffery and Wilson (eds.), New York, Plenum Press, 1990, p. 195–204], locust *Locusta migratoria* (Holman et al., 1990, ibid), corn earworm *Helicoverpa zea* (Blackburn et al., 1995, J. Insect Physiol. 41:723–730) as well as mosquitos *Culex salinarius* (Hayes et al., 1994, Regul. Rept. 52:235–248) and *Aedes aegypti* [Veenstra, 1994, Biochem. Biophys. Res. Commun. 202:715–719). Although the first members of this peptide family were isolated on the basis of their ability to stimulate contractions of the isolated cockroach hindgut (Holman et al., 1987, ibid), they have also been associated with diuretic activity in the cricket and mosquito. The Leucophaea cockroach hindgut preparation is extremely sensitive to these myotropic peptides, with thresholds in the range between $10^{-10}$ and $10^{-11}$M (Nachman and Holman, Myotropic insect neuropeptide families from the cockroach *Leucophaea madera:* Structure-activity relationships, In: Insect neuropeptides: Chemistry, biology, and action, Menn and Masler (eds.), Washington, D.C., American Chemical Society, 1991, p. 194–214). Hayes et al. (1989, Life Sci. 44:1259–1266) have reported that leucokinins influence transepithelial membrane potential and rate of fluid secretion in isolated Malpighian tubules from the mosquito, *Aedes aegypti*. Coast et al. [1990, J. Insect Physiol. 36(7):481–488] have shown that the achetakinins at $10^{-9}$M double the rate of fluid secretion by isolated Malpighian tubules of the cricket, *Acheta domesticus* and demonstrate EC$_{50}$ values between $10^{-10}$ and $10^{-11}$M. Therefore, this family of peptides may regulate water and ion balance in addition to hindgut motility in insects.

Utilizing an antibody to cockroach leucokinin I, a group of efferent neurons was stained in abdominal ganglia of flies (Cantera and Nässel, 1992, Cell Tissue Res. 269:459–471), the cockroach *Leucophaea maderae* (Nässel et al., 1992, J. Comp. Neurol. 322:45–67), and in larvae of several lepidopteran species (Cantera et al., 1992, Cell Tissue Res. 269:65–77). In the moth *Agrotis segetum*, leucokinin-immunoreactive fibers innervating the parasympathetic organs form an elaborated plexus extending over most of the abdominal nerve cord. Nässel et al. (Nässel et al., 1992, ibid) suggest that if leucokinins regulate hindgut contractility in *Leucophaea maderae*, they probably act as neurohormones, because leucokinin-immunoreactive neurons form a substantial supply of axons to the storage lobe of the corpora cardiaca, but the hindgut is not directly innervated by leucokinin-immunoreactive fibers.

The C-terminal pentapeptide sequence common to the insect kinins is all that is required to elicit a physiological response in myotropic and diuretic assays. In particular, the active core sequence Phe—Tyr—Pro—Trp—Gly—NH$_2$ is equipotent with the parent nonapeptide in hindgut myotropic (Holman et al., 1987, ibid) and cricket Malpighian tubule secretion [Coast et al., 1990, ibid) assays. Within the active core pentapeptide, the aromatic residues Phe$^1$ and Trp$^4$ are of paramount importance for activity in both bioassay systems, whereas position 2 tolerates wide variations in side-chain character ranging from acidic to basic or hydrophobic to hydrophilic (Nachman and Holman, 1991, ibid; Nachman et al., 1993, Arch. Insect Biochem. Physiol. 22:181–197). Aromatic residues, such as Tyr or Phe, in the variable position 2 promote the highest potencies in myotropic and Malpighian tubule fluid secretion assays [Nachman and Holman, 1991, ibid; Nachman et al., 1993, ibid; Nachman et al., Pseudopeptide mimetic analogs of insect neuropeptides, In: Natural and derived pest management agents, Hedin et al. (eds.), Washington, D.C., American Chemical Society, 1994, p. 210–229]. Spectroscopy, coupled with molecular dynamic studies on an active, conformationally restricted cyclic hexapeptide analogue of the insect kinins, suggests that the peptides adopt a turn conformation involving the Pro residue in the active core region during receptor interaction [Nachman et al., Incorporation of chemical/conformational components into mimetic analogs of insect neuropeptides, In: Insects: chemical, physiological and environmental aspects, Konopinska et al. (eds.), Wroclaw, Wroclaw University Press, 1995, p. 51–60; Nachman et al., Concensus chemistry and conformation of an insect neuropeptide family analogous to tachykinins, In: Progress in comparative endocrinology, Epple et al. (eds.), New York, Willey-Liss, Inc., 1990, p. 60–66; Roberts et al., Chemistry and Biology, in press].

Recent experiments demonstrate that several members of the insect kinin family are hydrolysed, and therefore inactivated, by angiotensin converting enzyme (ACE) from the housefly via removal of the C-terminal dipeptide amide fragment. Inactivation results because the hydrolysis site is located within the insect kinin C-terminal pentapeptide active core. In mammals, the Zn$^{2+}$ metallopeptidase ACE is responsible for the conversion of angiotensin I to the active form angiotensin II, involved in the control of blood pressure. In addition, ACE inactivates a wide range of mammalian peptide hormones bradykinin, cholecystokinin, [Leu$^5$] and [Met$^5$]enkephalinamides, substance P, and LH-RH (Gregory et al., 1964, Nature 204:931–933; Lamango et al., Peptides, submitted). The broad substrate specificity and widespread distribution of ACE in mammalian tissues suggests that it plays multiple roles in addition to controlling blood pressure, although these roles have yet to be defined. Similarly, the precise role of ACE has not been delineated in insects. However, the fact that a number of different C-terminally amidated insect neuropeptides are substrates of, and thereby inactivated by, housefly ACE (Gregory et al., 1964, ibid; Lamango et al., ibid) suggests that the endopeptidase may play a role in the degradation of regulatory peptides in insects.

Members of the insect kinin class of peptides can influence cockroach hindgut motility, fluid secretion in the Malpighian tubules of crickets, locusts and mosquitos, and ion balance. However, they are unsuitable as pest insect control agents and/or research tools for insect neuroendocrinologists due, in large measure, to susceptibility to both exopeptidases and endopeptidases in the hemolymph and gut of the insect.

The contents of each of the above-mentioned publications are incorporated by reference herein.

SUMMARY OF THE INVENTION

We have discovered novel pseudopeptide analogs of the insect kinin neuropeptide family which possess biological activity mimicking that of the naturally occurring neuropeptides. By substituting a sterically hindered amino acid which is compatible with a turn conformation, for the $Xaa^2$ (i.e. Ser, Pro, or Ala) amino acid of the insect kinin C-terminal pentapeptide, analogs are produced which exhibit resistance to degradation by angiotensin converting enzyme (ACE) while still retaining biological activity. The analogs may be used for insect control by disrupting the diuretic and/or myotropic activity in insects.

In accordance with this discovery, it is an object of this invention to provide novel compounds having biological activity mimicking that of the naturally occurring insect kinin neuropeptides.

It is also an object of this invention to provide compounds which are bioactive mimics of insect kinin neuropeptides that are resistant to enzymatic degradation.

Another object is to provide compounds which are bioactive mimics of insect kinin neuropeptides and their use for controlling insect populations.

Other objects and advantages of the invention will become readily apparent from the ensuing description.

DETAILED DESCRIPTION OF THE INVENTION

Figure 1:
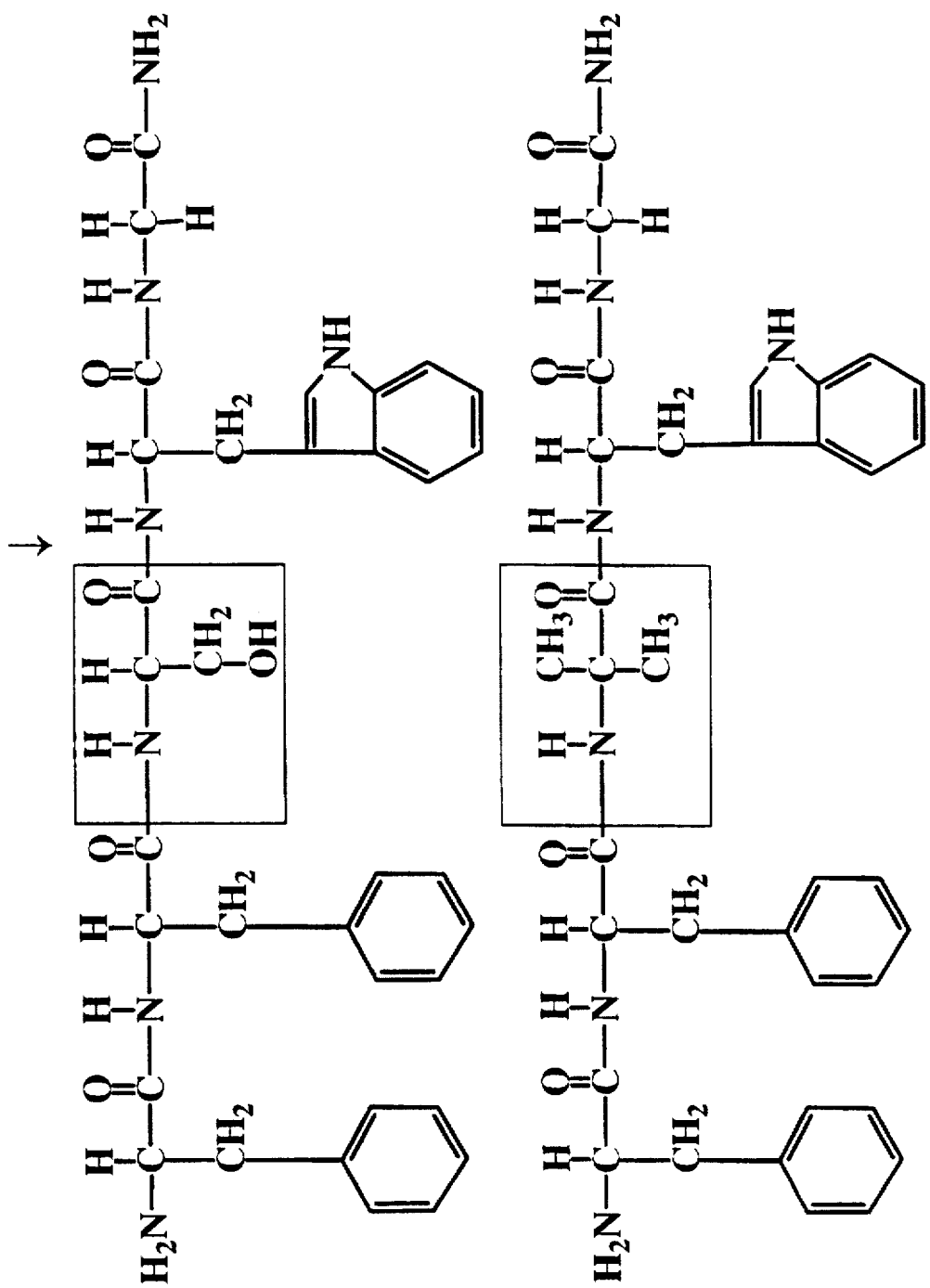
FIG. 1 shows the naturally occurring insect kinin C-terminal pentapeptide and its analog. The naturally occurring insect kinin C-terminal pentapeptide Phe—Phe—Ser—Trp—Gly—$NH_2$ is pictured at the top. The arrow indicates the point at which the insect kinins are hydrolyzed, and therefore inactivated, by the endopeptidase angiotensin converting enzyme (ACE) from the housefly *Musca domestica*. The insect kinin analog Phe—Phe—Aib—Trp—Gly—$NH_2$ (bottom) features a replacement of the Ser (or Pro) in the pentapeptide core with the sterically hindered aminoisobutyrl (Aib) residue and demonstrates both complete resistance to ACE and stimulation of fluid secretion in the Malpighian tubules of the cricket *Acheta domesticus* with greater potency than the endogenous insect kinins.

In the following description, the nomenclature used to define the peptides and pseudopeptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The compounds of the invention are prepared from any insect kinin containing the C-terminal pentapeptide Phe—$Xaa^1$—$Xaa^2$—Trp—Gly—$NH_2$ ($Xaa^1$=His, Asn, Phe, Ser, or Tyr; $Xaa^2$=Ser, Pro, or Ala), or a bioactive C-terminal portion thereof containing this same C-terminal pentapeptide. We have found that by substituting a sterically hindered amino acid which is compatible with a turn conformation for the $Xaa^2$ amino acid within the insect kinin C-terminal pentapeptide, analogs are produced which are resistant to degradation by the angiotensin converting enzyme (ACE) but which still retain biological activity.

The compounds of this invention are of the general Formula I:

R—$X_1$—$X_2$—Trp—Gly—$NH_2$ (I)

where $X_1$ is Asn, His, Phe, Ser, or Tyr, and the $X_2$ moiety is the amino acid effective to impart steric hindrance to ACE while still retaining the turn conformation of the native $Xaa^2$ amino acid. The moieties R and $X_2$ are described in greater detail hereinbelow.

In the preferred embodiment, the $X_2$ moiety is an amino acid having the structure:

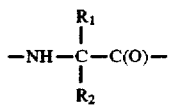

where $R_1$ and $R_2$ are hydrocarbons independently selected from -alkyl and -alkylphenyl moieties. Suitable alkyl groups include short chain alkyl hydrocarbons which may be branched or straight chain, while the phenyl group may be optionally substituted with one or more other short chain alkyl hydrocarbons. Either or both of the alkyl and phenyl groups (including any alkyl substituents on the phenyl group) may be optionally halogenated to increase hydrophobicity. A variety of short chain hydrocarbons, including those directly bonded to the α-C of the amino acid as well as any optional substituents on the phenyl group, may be used herein. However, to retain the turn conformation and thus the bioactivity of the C-terminal pentapeptide, the short chain hydrocarbon joined to the α-C of the amino acid should be less than or equal to four C long. Preferred short chain hydrocarbons include but are not limited to —$CH_3$, —$CH_2X$, —$CHX_2$ and —$CX_3$, wherein X is F, Cl, Br or I.

The analog of this invention may be prepared from any member of the insect kinin family of neuropeptides containing the above-mentioned C-terminal pentapeptide, Phe—$Xaa^1$—$Xaa^2$—Trp—Gly—$NH_2$. A variety of these insect kinins have been previously described and are suitable for use herein. As mentioned, the kinin polypeptide which is modified to incorporate the $X_2$ amino acid should include at least an active C-terminal portion containing this pentapeptide, and may encompass the entire native insect kinin polypeptide or only a bioactive portion thereof. Thus, in the first embodiment, R in formula (I) may then be shown as:

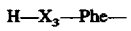

H—$X_3$—Phe— wherein $X_3$ is a bond, or an amino acid or polypeptide which is all or a portion of an insect kinin neuropeptide that is naturally contiguous to the terminal Phe of the C-terminal pentapeptide. In other words, in this embodiment, the R group may be simply Phe (as is found in the naturally occurring C-terminal pentapeptide), or Phe bonded to an amino acid or polypeptide which is contiguous to this same Phe in naturally occurring insect kinins.

Although the R group of the compound may be as described above, in accordance with alternative embodiments, the insect kinins may be further modified to incorporate a hydrophobic moiety into the R group to render the compounds more hydrophobic and/or amphiphilic. In another alternative, the analogs may be further modified to incorporate an aminopeptidase protecting moiety into the R group to provide additional protection from enzymatic degradation. By also adding a hydrophobic moiety to the compound, insect kinin analogs are produced which are capable of penetrating the insect cuticle while still retaining bioactivity. The modification of insect neuropeptides of the pyrokinin/PBAN family to incorporate amphiphilic moieties for this purpose was described in our U.S. patent application Ser. No. 08/700,915 ("Mimetic Insect Pyrokinin Analogs for Insect Control", filed Aug. 22, 1996), the contents of which are incorporated by reference herein. These same modifications may be applied to the insect kinin neuropeptides of this invention.

Accordingly, in a second preferred embodiment, the compound is a pseudotetrapeptide analog of the C-terminal insect kinin core region. In this embodiment, a hydrophobic carborane moiety is incorporated as a replacement for the phenyl ring of the amino acid Phe of the modified C-terminal pentapeptide, Phe—$X_1$—$X_2$—Trp—Gly—$NH_2$. Specifically, o- or m-carborane conjugated to a short chain alkanoyl-acyl group is substituted for the N-terminal Phe. Referring to Formula I, R may be shown as:

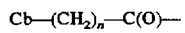

where Cb is a carborane, and n is 1, 2 or 3. In a variation of this embodiment, the N-terminal Phe of the pentapeptide may be replaced with hydrocinnamic acid rather than the carborane moiety.

In a third preferred embodiment, the insect kinins or at least an active C-terminal portion thereof containing the modified C-terminal pentapeptide Phe—$X_1$—$X_2$—Trp—Gly—$NH_2$, is further modified at its N-terminus by addition of a hydrophobic moiety which may be an aromatic amine or aromatic acid, or by addition of an aminopeptidase protecting moiety such as pyroglutamic acid as described by Gregory (1964, Nature, 204:931–933). A variety of aromatic amines and acids are suitable for use herein. Preferred acids include phenyl alkanoic, alkenoic or alkynoic acids such as 6-phenyl hexanoic acid and 9-phenyl nonanoic acid, while preferred amines include phenyl alkanoic, alkenoic or alkynoic amines such as 4-phenyl butyl amine. Without being limited thereto, examples of other suitable aromatic acids include 2-biphenylenecarboxylic acid, 9-anthracenecarboxylic acid, 9-fluoreneacetic acid, 1-fluorene carboxylic acid, and 1-pyrenebutyric acid, while other suitable aromatic amines include 1-aminoanthracene, 6-amino-3,4-benzocoumarin, 2-amino-7-bromofluorene, 6-aminochrysene, 3-aminofluoranthene, 9-aminophenanthrene, and 1-pyrenemethylamine.

The analog of this third embodiment may also be prepared from any member of the insect kinin family of neuropeptides. As mentioned, the kinin polypeptide to which the hydrophobic moiety or pyroglutamic acid is attached should include at least an active C-terminal portion containing the modified C-terminal pentapeptide Phe—$X_1$—$X_2$—Trp—Gly—$NH_2$, and may encompass the entire native insect kinin polypeptide. However, when using the hydrophobic moieties of this embodiment, the polypeptide should not be so large as to lose the hydrophobic character introduced by the moiety. Thus, particularly when preparing analogs of larger insect kinins, best results are achieved when only using a C-terminal portion of the molecule. Thus, without being limited thereto, the size of the polypeptide (including the above-mentioned modified C-terminal pentapeptide) is preferably less than or equal to about 10 to 12 amino acids. Conversely, the skilled practitioner will recognize that when using smaller insect kinin neuropeptides, including but not limited to the nonapeptide of the cricket *Acheta domesticus*, the entire polypeptide may be used.

The above-mentioned hydrophobic aromatic acids or amines, or pyroglutamic acid, may be conjugated to the modified insect kinin peptide directly or through an optional spacer. Use of the spacer is preferred with use of the aromatic acids or amines however, to minimize any steric hindrance of the active polypeptide portion of the compound by the hydrophobic moiety and inhibition of receptor binding. The structure of the spacer will vary with the particular hydrophobic group. Without being limited thereto, when the hydrophobic moiety is an aromatic acid, preferred spacers may be non-polar hydrocarbons having a free amino group and free carboxyl group, or relatively non-polar or uncharged α-amino acids, such as Ala or Gly. When using an aromatic amine as the hydrophobic moiety, preferred spacers are hydrocarbon diacids, such as succinic acid. Other specific spacers may be readily determined by the practitioner skilled in the art.

In summary, in accordance with the structure shown in Formula (I), the structure of R for the third embodiment may be shown as:

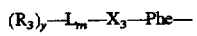

where $R_3$ is the hydrophobic moiety or pyroglutamic acid, y is 1 or 2 (preferably 1 when $R_3$ is a hydrophobic moiety), m is 0 or 1, and L is the spacer. As in the first embodiment, the group $X_3$ may be a bond, or an amino acid or polypeptide which is naturally contiguous to the C-terminal pentapeptide —Phe—$Xaa^1$—$Xaa^2$—Trp—Gly—$NH_2$.

The peptides and pseudopeptide analogs of this invention may be synthesized by a variety of conventional methods, such as exclusively solid-phase techniques, partial solid-phase techniques, fragment condensation, or classical solution addition. The peptides may also be synthesized by recently developed recombinant DNA techniques which may be utilized for large-scale use in the field with the purpose of controlling insect populations to prevent crop damage and/or the spread of disease.

As stated above, the compounds of Formula I can be synthesized by methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105–253 (1976)], or solid phase synthesis [see Barany and Merrifield, In "The Peptides," Vol. 2, E. Gross and J. Meienhofer (eds.), Academic Press, New York, pp. 3–284 (1979)], or stepwise solid phase synthesis as reported by Merrifield [J. Am. Chem. Soc. 85: 2149–2154 (1963)], the contents of each of which are incorporated herein by reference. In the preferred embodiment, the kinin polypeptides and the analogs may be synthesized using the same solid phase techniques described by Nachman et al. (1995, Reg. Peptides, 57:359–370) or Christensen et al. (1991, Proc. Natl. Acad. Sci., USA, 88:4971–4975), the contents of each of which are incorporated by reference herein.

As a practical matter it is anticipated that compositions of the pseudopeptide analogs would be prepared by formulating the compounds with an agriculturally acceptable inert carrier, particularly a solvent suitable for topical applications. Although a variety of solvents may be used, alcohols such as ethanol or butanol are preferred. The compounds may also be formulated with solid inert carriers such as talc, clay or vermiculite, or incorporated into conventional controlled release microparticles or microcapsules. In addition, it is envisioned that the analogs may be optionally formulated in combination with conventional insect attractants, or other chemical or biological insecticides.

The pseudopeptide analogs of Formula (I) mimic the biological activity of the naturally occurring insect kinin neuropeptides and may induce a physiological response following application to an insect. Specifically, these compounds are effective for the stimulation or induction of diuretic and/or myotropic activities in various insect species. In practice, application of the compounds stimulates hindgut contraction (myotropic activity) in susceptible insects, causing premature voiding of digestive contents and nutrients. As a consequence, development may be disrupted and the pest weakened, increasing its susceptibility to pesticides, harmful environmental conditions and disease, and may eventually cause death. Furthermore, the compounds may also upset the cellular water and ion balance within susceptible pests, again weakening or killing the treated insects.

Depending upon the pest species, the concentration of the agent, and method of application, the analogs act to control pests by one or more of the above-mentioned mechanisms. Accordingly, the compounds are administered in an amount effective to induce one or more of these responses as determined by routine testing. For example, where the desired effect is stimulation of myotropic activity, an "effective amount" is defined to mean those quantities which will result in a significant increase in hindgut contraction in a test group as compared to an untreated control. Similarly, where the ultimate response is pest mortality, an "effective amount" or "pesticidally effective amount" is defined to mean those quantities which will result in a significant mortality rate of a test group as compared to an untreated group. The actual effective amount will of course vary with the specific compound, the target insect and its stage of development, the application technique, the formulation, the level of any additional insecticide, the desired effect, and the duration of the effect, and may be readily determined by the practitioner skilled in the art. For example, when the compounds are to be orally ingested or injected, the effective amounts may be significantly reduced.

The pseudopeptide analogs of this invention may be applied directly to the target insects (i.e., larvae, pupae and/or adults), or to the locus of the insects. In accordance with the first embodiment, wherein no hydrophobic moieties have been incorporated into the compound to render it more hydrophobic and/or amphiphilic, the compounds may be administered either subcutaneously, percutaneously, or orally. When they are to be ingested, they should be applied with their carrier to the insect diet. Alternatively, because the compounds of the second and third embodiments (having hydrophilic moieties incorporated therein) will penetrate the insect cuticle they are preferably administered topically, such as by direct spraying on the insect or a substrate which is likely to be contacted by the insect. The compounds may be applied continuously or semicontinuously, or they may be formulated in timed or continuous release carriers for sustained release over time.

The compounds encompassed herein are effective for controlling a broad spectrum of insects. Without being limited thereto, it is envisioned that pests of interest which may be controlled are agronomically or commercially important insects, including locusts, grasshoppers, mosquitos, the corn earworm, and cockroaches. The compounds may be particularly effective against the locust, *Locusta migratoria*, the mosquitos *Culex salinarius* and *Aedes aegypti*, the corn earworm, *Helicoverpa zea*, and the cockroach, *Leucophaea maderae*. Although of lesser significance, the compounds may also be effective against crickets, including *Acheta domesticus*.

The following examples are intended only to further illustrate the invention and are not intended to limit the scope of the invention which is defined by the claims.

EXAMPLE 1

In these examples we describe the synthesis of several analogs of the insect kinin C-terminal pentapeptide core, containing the sterically-hindered aminoisobutyric acid (Aib) residue, that display potent diuretic activity in the cricket *Acheta domesticus* and complete resistance to the endopeptidase ACE. Two of the analogs are also blocked at the N-terminus with pyroglutamic acid (pGlu) residues, which confer resistance to an additional class of peptidases, the aminopeptidases.

Materials and Methods

Peptide Analog Synthesis

The peptide analogs were synthesized via FMOC methodology on Rink Amide resin (Novabiochem, San Diego, Calif.) and using FMOC protected amino acids (Advanced Chemtech, Louisville, Ky.). The side chain of Lys in the synthesis of pGlu—Lys—Phe—Phe—Aib—Trp—Gly—$NH_2$ was protected with a tBOC group, whereas it was protected with an FMOC group in the synthesis of pGlu—Lys(pGlu)—Phe—Phe—Aib—Trp—Gly—$NH_2$. Coupling reagents used for the majority of amino acid condensations were 1 eq. of 1,3-diisopropylcarbodiimide/1-hydroxy-7-azabenzotriazole (HOAt) mixture in dimethylsulfoxide for 2 hours according to previously described procedures (Nachman et al., 1995, Peptides, 16:809–813, the contents of which are incorporated by reference herein). However, for coupling of the Aib residue and the residue immediately following Aib to the peptide-resin complex the reagent utilized was 1 eq. [O-(7-Azabenzotriazol-1-yl)-1,1,3,3-tetramethyluronium hexafluorophosphate] (HATU) (PerSeptive Biosystems, Marlborough, Mass.) with 2 eq. N,N-diisopropylethylamine in dimethylsulfoxide for 4 hours. Removal of the N-terminal FMOC group from the Aib group was accomplished with 20% piperidine in dichloromethane for 1 hour rather than the 30 min used for the other residues. The product was cleaved from the resin by stirring the peptide-resin complex with a mixture of trifluoroacetic acid (90%))/anisole (5%)/thioanisole (4%)/1,2-ethanedithiol (1%) for 1.5 hours at ambient temperature. The resin suspension was filtered and volatile reagents removed in vacuo on a Savant (Farmingdale, N.Y.) Speed Vac concentrator at 40° C. The crude product was purified on a Waters C18 cartridge and a Delta Pak C18 reverse phase column on a Waters Model 510 HPLC controlled with a Millenium 2010 chromatography manager system (Waters, Milford, Mass.) with detection at 214 nm at ambient temperature; Solvent A=0.1% aqueous trifluoroacetic acid (TFA); Solvent B=80% aqueous acetonitrile containing 0.1% TFA. Conditions: Initial solvent consisting of 20% B was followed by Waters linear program 6 to 100% B over 40 min; flow rate 2 ml/min. Retention times: Phe—Phe—Aib—Trp—Gly—$NH_2$, 25.5 min; pGlu—Lys—Phe—Phe—Aib—Trp—Gly—$NH_2$, 23.2 min; pGlu—Lys(pGlu)—Phe—Phe—Aib—Trp—Gly—$NH_2$, 24.7 min. Final purification took place on a Waters Protein Pak 125 column. Solvent A=95% acetonitrile containing 0.01% TFA, Solvent B=50% acetonitrile containing 0.01% TFA. Conditions: 100% A isocratic for 4 min followed by linear program to 100% B over 8 min. Retention times: Phe—Phe—Aib—Trp—Gly—$NH_2$, 13.5 min; pGlu—Lys—Phe—Phe—Aib—Trp—Gly—$NH_2$, 21.6 min; pGlu—Lys(pGlu)—Phe—Phe—Aib—Trp—Gly—$NH_2$, 22.8 min. The pure peptides were analyzed and quantitated via amino acid analysis under previously described conditions (Nachman et al., 1995, Peptides, 16:809–813), revealing the following analyses: Phe—Phe—Aib—Trp—Gly—NH$_2$: F(2.1), G(0.9); pGlu—Lys—Phe—Phe—Trp—Gly—NH$_2$: E(0.9), F(2.0), G(0.9), K(0.8); pGlu—Lys(pGlu)—Phe—Phe—Aib—Trp—Gly—NH$_2$: E(2.2), F(2.0), G(0.9), K(1.0). Fast atom bombardment (FAB) mass spectra were obtained by adding 10 μg of peptide sample to glycerol (1.5 μL) on a copper probe, followed by bombardment with 8KV Xe atoms on a Kratos MS- 50 mass spectrometer (Kratos, Manchester, UK). The structural identity and a measure of the purity of the peptides were confirmed by the presence of the following molecular ions (MH$^+$): Phe—Phe—Aib—Trp—Gly—NH$_2$, 640.4 (Calcd. MH$^+$: 640.32); pGlu—Lys—Phe—Phe—Aib—Trp—Gly—NH$_2$, 879.5 (Calcd. MH$^+$: 879.45); pGlu—Lys(pGlu)—Phe—Phe—Aib—Trp—Gly—NH$_2$, 990.9 (Calcd. MH$^+$: 990.75).

Cricket Malpighian Tubule Secretion Bioassay

Crickets were reared as described (Clifford et al., 1977, Ann. Entomol. Soc. Am., 70:69–74) and fed a diet of turkey starter crumbs. Water was provided ad lib. Malpighian tubules were removed from 6–12-day-old adult virgin females. Single tubules were isolated in vitro as described (Coast, G. M., 1988, Physiol. Entomol., 13:381–391). After a 40-min equilibration period, the bathing fluid was changed and the rate of secretion, in picoliters per millimeter length of tubule per minute (pl/mm/min), was determined over 40 min (control rate). Thereafter, the bathing fluid was exchanged for one containing the assay material and the rate of secretion was determined over an additional 40-min period (experimental rate). Diuretic activity was calculated as the difference between control and experimental rates, and results are expressed as a percentage of the response obtained with a supermaximal dose (10 nM) of achetakinin-I assayed alongside the test analogues. All experiments were performed at room temperature (21°–24° C.) (Coast et al., 1990, ibid).

Cockroach Myotropic Biossay

*Leucophaea maderae* cockroaches were taken from stock colonies maintained at 27° C. and fed dry dog food ad lib. Cockroach hindguts, free of central nervous system (CNS) tissue, were dissected, immersed in saline, and prepared for recording of myogenic activity as previously described [Holman et al., 1991, Insect Biochem., 21(1):107–112]. Threshold concentrations were determined for each analogue by adding a known quantity of peptide (dissolved in 0.5 ml bioassay saline) to the bioassay chamber containing the hindgut and observing the response on a Gould 2200S oscillograph recorder. The quantity of the peptide analogues was calculated from the values obtained for Phe in the amino acid analysis. The threshold concentration was defined as the minimum concentration of peptide in the chamber required to evoke an observable change in the frequency (50%) or amplitude of contractions (5%) within 1 min and sustained for 3 min. Threshold concentrations were obtained from five cockroach hindguts on 5 consecutive days for each peptide. Quantitative data for dose-response plots were obtained as previously described (Holman et al., 1991, ibid).

ACE Enzyme Trials

Musca ACE (Mr, 67,000) was purified from a soluble extract of adults as described elsewhere (Cornell et al., J. Biol. Chem., in press; Lamango and Isaac, J. Biol. Chem., in press) and yielded enzyme which appeared as a single band by SDS-PAGE. Unless otherwise stated, peptides (12–750 μM, final concentration) were incubated with Musca ACE in 100 mM Tris/HCl, pH 8.3 in the presence of 10 μM ZnCl$_2$ and 0.3M NaCl at 37° C. Reactions (15 μl) were terminated either by heating to 100° C. for 5 min or by the addition of 5 μl of 8% (v/v) TFA, followed by centrifugation (13000 g, Microcentaur) for 2 min and diluted to 100 μl with 0.1% (v/v) TFA before HPLC analysis.

HPLC analysis was performed using a Pharmacia Super-Pac Pep-S column (250 mm×4 mm, internal diameter) packed with 5 μm ODS particles. The solvent system comprised elution with 5% acetonitrile in 0.1% (v/v) trifluoroacetic acid for 3 min, followed by a linear increase of the acetonitrile component from 3 to 41% in 11 min (total run time of 14 min).

Results

The three Aib-containing insect kinin analogs Phe—Phe—Aib—Trp—Gly—NH$_2$ (FIG. 1), pGlu—Lys—Phe—Phe—Aib—Trp—Gly—NH$_2$, and pGlu—Lys(pGlu)—Phe—Phe—Aib—Trp—Gly—NH$_2$ demonstrated potent stimulation of fluid secretion on the isolated Malpighian tubules of the cricket *Acheta domesticus*, with EC$_{50}$ values of 5.6 pM (95% CL=3.0–10.5 pM), 2.8 pM (95% CL=2.1–3.8 pM) and 8.3 pM (95% CL=5.6–12.3 pM), respectively (Table 1). All produce a maximal diuretic response which was not significantly different from that obtained with the endogenous achetakinin peptides. The natural achetakinins elicit cricket Malpighian tubule secretion at EC$_{50}$ values ranging from about 20 to 325 pM (Table 1) (Coast et al., 1990, ibid). The three analogs are therefore about two to eight times more potent in the Malpighian tubule assay than the most potent naturally occurring achetakinin peptide. On the isolated *Leucophaea maderae* cockroach hindgut bioassay, the three Aib-containing analogs demonstrated threshold activities of 1.0×10$^{-10}$M, 3.5×10$^{-12}$M, 2.8×10$^{-8}$M, respectively (Table 1). The endogenous achetakinins stimulate spontaneous contractions of the cockroach hindgut at threshold concentrations of between about 43 pM to 270 pM (Table 1) (Holman et al., 1990, ibid). The analogs are therefore roughly half as potent, an order of magnitude more potent, and three orders of magnitude less potent, respectively, than the most potent of the achetakinins in the cockroach hindgut myotropic assay.

Figure 2:
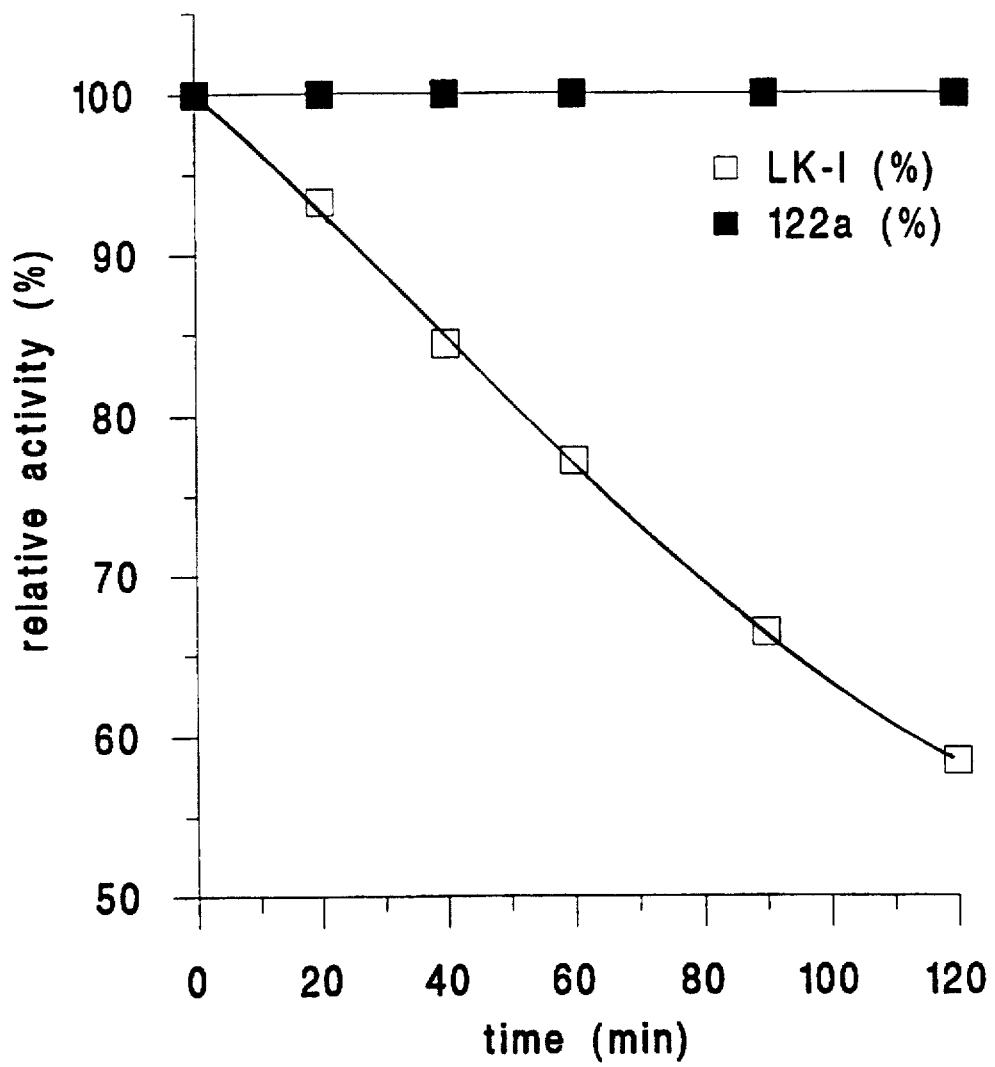
FIG. 2 shows the results of the hydrolysis trials with angiotensin converting enzyme (ACE) from the housefly *Musca domestica* on the naturally occurring insect kinin leucokinin I (LK-I: DPA—Phe—Asn—Ser—Trp—Gly—$NH_2$ (□) and the Aib-containing insect kinin analog Phe—Phe—Aib—Trp—Gly—$NH_2$ (■). The analog demonstrates complete resistance to hydrolysis by ACE.

All three peptide analogs demonstrated complete resistance to hydrolysis by angiotensin converting enzyme (ACE) from the housefly *Musca domestica* over 120 minutes, an incubation period sufficient to hydrolyze much of the natural insect kinin leucokinin I (LK-I) (FIG. 2). The sequence of LK-I is Asp—Pro—Ala—Phe—Asn—Ser—Trp—Gly—NH$_2$, which shares with achetakinin IV (AK-IV) an Asn residue in the variable X position of the C-terminal pentapeptide core region (Nachman and Holman, 1991, ibid). ACE also has been shown to hydrolyze the insect kinins (LK-II (DPG—Phe—Ser—Ser—Trp—Gly—NH$_2$), Cus-DP-I (QP—Phe—His—Ser—Trp—Gly—NH$_2$), Cus-DP-II (NNANV-Phe—Tyr—Pro—Trp—Gly—NH$_2$), and Cus-DP-III (SKYVSQK-Phe—Phe—Ser—Trp—Gly—NH$_2$) (Lamango et al., Peptides, submitted). It should be noted that Cus-DP-II contains a Pro residue in the third position of the pentapeptide core region, as do 3 of the 5 achetakinins (Table 1).

Discussion

Despite the incorporation of steric bulk at an alpha-carbon within the C-terminal pentapeptide core region, the three Aib-containing insect kinin analogs Phe—Phe—Aib—

Trp—Gly—NH₂, pGlu—Lys—Phe—Phe—Aib—Trp—Gly—NH₂ and pGlu—Lys(pGlu)—Phe—Phe—Aib—Trp—Gly—NH₂ demonstrate significant myostimulatory activity on the isolated *Leucophaea maderae* cockroach hindgut and potent stimulation of Malpighian tubule fluid secretion in the cricket, *Acheta domesticus* (Table 1). Molecular dynamics and NMR analysis of an active conformationally-restricted, cyclic insect kinin analog, demonstrates the importance of a beta-turn involving the Pro (or Ser) residue within the active core region for successful receptor interaction [Nachman et al., Incorporation of chemical/conformational components into mimetic analogs of insect neuropeptides, In: Insects: chemical, physiological and environmental aspects, Konopinska et al. (eds.), Wroclaw, Wroclaw University Press, 1995, p. 51–60; Roberts et al., Chemistry and Biology, in press]. The Aib residue is compatible with the formation of a turn at this position. Unfavorable steric interactions between the branched chain of the Aib alpha carbon and side chains of surrounding residues promote the formation of a turn or kink to alleviate strain [Tallon et al., 1983, Biopolymers 33:915–926; Toniolo et al., 1983, Biopolymers 22:205–214). This characteristic may explain, at least in part, the potent biological activities observed for these kinin analogs.

In the cockroach hindgut myotropic bioassay, the first analog is one half as potent as achetakinin IV (AK-IV), among the most potent of the naturally occurring insect kinins of the cricket and/or cockroach [Nachman and Holman, 1991, ibid). The second analog is an order of magnitude more potent, while the third di-pGlu analog is three orders of magnitude less potent than AK-IV in the cockroach hindgut myotropic bioassay. The presence of the Lys residue in the mono-pGlu analog probably accounts for the superagonist activity in the myotropic assay, because the insect kinin hexapeptide analog Lys—Phe—Phe—Pro—Trp—Gly—NH₂ is also more active than the pentapeptide core and/or the naturally occurring insect kinins (Nachman et al., 1994, ibid). The drop in activity observed for the di-pGlu analog is apparently due to the detrimental steric effect of the pGlu attached to the Lys side chain on receptor interaction.

In the cricket Malpighian tubule fluid secretion assay, the three Aib analogs demonstrate similar potencies at a level two to eight fold more active than AK-IV (Table 1), one of the most potent of the insect kinins found in the cricket (Nachman and Holman, 1991, ibid). In contrast with the cockroach hindgut myotropic assay, the presence of the pGlu on the Lys side chain in the di-pGlu analog does not cause a statistically significant drop in fluid secretion activity in the isolated Malpighian tubules of the cricket.

While the steric bulk in the backbone of the Aib-containing analogs does not impede interaction with the insect kinin receptors on the cockroach hindgut or cricket Malpighian tubule, it does prevent the endopeptidase ACE from hydrolyzing and inactivating the kinin core region. Presumably, the branched chain at the alpha carbon of Aib (FIG. 1) prevents complete binding with the enzyme. The two analogs blocked at the N-terminus with pGlu are protected from aminopeptidase attack as well (Gregory et al., 1964, ibid).

It is understood that the foregoing detailed description is given merely by way of illustration and that modifications and variations may be made therein without departing from the spirit and scope of the invention.

TABLE 1

Comparison of the cricket Malpighian tubule secretion and cockroach hindgut myotropic activity of the Aib-containing insect kinin analogs and naturally occurring achetakinins

| | | Cricket (*Acheta domesticus*) Malpighian tubule fluid secretion | | Cockroach (*Leucophaea maderae*) |
|---|---|---|---|---|
| | Peptide Analog | EC₅₀ (pM) | Maximum response (%) | hindgut contraction threshold (pM) ± (S.D.) |
| AK-I: | SGAD—Phe—Tyr—Pro—Trp—Gly—NH₂ | 78 | 86 (6) | 82 ± 22 (12) |
| AK-II: | AY—Phe—Ser—Pro—Trp—Gly—NH₂ | 22 | 91 (6) | 48 ± 5 (12) |
| AK-III: | ALP—Phe—Ser—Ser—Trp—Gly—NH₂ | 324 | 108 (6) | 270 ± 28 (12) |
| AK-IV | NFK—Phe—Asn—Pro—Trp—Gly—NH₂ | 24 | 96 (6) | 180 ± 86 (12) |
| AK-V: | A—Phe—His—Ser—Trp—Gly—NH₂ | 18 | 88 (6) | 43 ± 5 (12) |
| | Phe—Phe—Aib—Trp—Gly—NH₂ | 5.6 | 99 | 100 ± 34 |
| | pQKPhe—Phe—Aib—Trp—Gly—NH₂ | 2.8 | 101 | 3.5 ± 0.7 |
| | pQK(pQ)Phe—Phe—Aib—Trp—Gly—NH₂ | 8.3 | 103 | 28,000 ± 11,000 |

We claim:

1. A compound of the formula

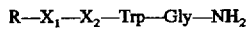

wherein:

(a) X₁ is selected from the group consisting of Asn, His, Phe, Ser and Tyr;

(b) X₂ is an amino acid having the structure:

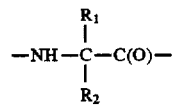

where R₁ and R₂ are hydrocarbon groups independently selected from the group consisting of -alkyl and -alkylphenyl, where said alkyl comprises optionally halogenated alkyl hydrocarbon groups which may be branched or straight chain, and said phenyl may be optionally substituted with one or more halogens and/or other optionally halogenated alkyl hydrocarbon groups; and (c) R is selected from the group consisting of:
  (i) hydrocinnamic acid,
  (ii) Cb—(CH₂)ₙ—C(O)— where:
    (i) Cb is a carborane, and (ii) n is 1, 2, or 3;
(iii) H—$X_3$—Phe—, and
(iv) $(R_3)_y$—$L_m$—$X_3$—Phe—where:
  (i) $X_3$ is selected from the group consisting of a bond, an amino acid, and a polypeptide, said polypeptide comprising all or a portion of an insect kinin neuropeptide which is naturally contiguous to the C terminal pentapeptide —Phe—$X_1$—$X_4$—Trp—Gly—$NH_2$, where $X_4$ is Ala, Ser or Pro;
  (ii) $R_3$ is selected from the group consisting of hydrophobic aromatic amines, hydrophobic aromatic acids, and pyroglutamic acid, said hydrophobic aromatic amines and said hydrophobic aromatic acids being effective to render said compound hydrophobic or amphiphilic or both;
  (iii) y is 1 or 2;
  (iv) m is 0 or 1; and
  (v) L is a spacer which, when $R_3$ is a hydrophobic aromatic acid, said spacer is selected from the group consisting of non-polar hydrocarbons having a free amino group and free carboxyl group, and uncharged α-amino acids, or when $R_3$ is a hydrophobic aromatic amine, said spacer is a diacid.

2. The compound of claim 1 wherein $R_1$ and $R_2$ are short chain optionally halogenated alkyl hydrocarbons which may be branched or straight chain.

3. The compound of claim 1 wherein said short chain hydrocarbon contains between 1 to 4 C.

4. The compound of claim 1 wherein $R_1$ and $R_2$ are selected from the group consisting of —$CH_3$, —$CH_2X$, —$CHX_2$ and —$CX_3$, wherein X is F, Cl, Br or I.

5. The compound of claim 1 wherein $X_3$ is a bond and R is Phe—.

6. The compound of claim 1 wherein R is $(R_3)_y$—$L_m$—$X_3$—Phe—, $R_3$ is selected from the group consisting of said hydrophobic aromatic amines and said hydrophobic aromatic acids, and $X_3$ is all or a portion of a kinin neuropeptide which is naturally contiguous to said C terminal pentapeptide and is sufficiently small as to retain the hydrophobicity of said compound introduced by said hydrophobic aromatic amines or said hydrophobic aromatic acids.

7. The compound of claim 1 wherein R is $(R_3)_y$—$L_m$—$X_3$—Phe—, $R_3$ is said pyroglutamic acid, and $X_3$ is all or a portion of a kinin neuropeptide which is naturally contiguous to said C terminal pentapeptide.

8. The compound of claim 1 wherein R is H—$X_3$—Phe—, and $X_3$ is all or a portion of a kinin neuropeptide which is naturally contiguous to said C terminal pentapeptide.

9. The compound of claim 1 wherein R is $(R_3)_y$—$L_m$—$X_3$—Phe—, and $X_3$ is a bond.

10. The compound of claim 1 wherein R is $(R_3)_y$—$L_m$—$X_3$—Phe—, and $X_3$ is a polypeptide having less than or equal to about 7 amino acids.

11. The compound of claim 1 wherein R is said Cb—$(CH_2)_n$—C(O)—.

12. A composition comprising the compound of claim 1 and an inert carrier.

13. The composition of claim 12 wherein said carrier is an alcohol.

14. A method for controlling insects comprising applying the compound of claim 1 to the locus of said insects.

15. The method of claim 14 wherein said insects are selected from the group consisting of cockroaches, locusts, grasshoppers, mosquitos, and the corn earworm.

16. The method of claim 14 wherein said applying comprises topically applying said compound onto said insects.

17. The method of claim 14 wherein said compound is applied in an amount effective to stimulate diuretic activity in said insect.

18. The method of claim 14 wherein said compound is applied in an amount effective to stimulate gut contraction in said insect.

* * * * *